United States Patent [19]

Fetto

[11] Patent Number: 5,211,666
[45] Date of Patent: May 18, 1993

[54] HIP JOINT FEMORAL COMPONENT ENDOPROSTHESIS WITH A LATERAL LOAD-TRANSFERRING SUPPORT SURFACE

[75] Inventor: Joseph F. Fetto, New York, N.Y.

[73] Assignee: New York University, New York, N.Y.

[21] Appl. No.: 688,408

[22] Filed: Apr. 22, 1991

[51] Int. Cl.⁵ .............................. A61F 2/36
[52] U.S. Cl. .......................... 623/23; 623/18
[58] Field of Search ............ 623/22, 23, 16, 18

[56] References Cited

U.S. PATENT DOCUMENTS

| | | | |
|---|---|---|---|
| 3,806,957 | 4/1974 | Shersher | 623/23 |
| 3,863,273 | 2/1975 | Averill | 623/23 |
| 3,894,297 | 7/1975 | Mittelmeier et al. | 623/22 |
| 3,896,505 | 7/1975 | Timmermans | 623/23 |
| 3,995,323 | 12/1976 | Shersher | 623/23 |
| 4,031,571 | 6/1977 | Heimke et al. | 623/23 |
| 4,287,617 | 9/1981 | Tornier | 623/23 |
| 4,404,693 | 9/1983 | Zweymuller | 623/23 |
| 4,407,022 | 10/1983 | Heimke et al. | 623/23 |
| 4,530,114 | 7/1985 | Tepic | 623/23 |
| 4,549,319 | 10/1985 | Meyer | 623/22 |
| 4,608,053 | 8/1986 | Keller | 623/23 |
| 4,659,067 | 4/1987 | Fournier | 623/23 |
| 4,661,112 | 4/1987 | Muller | 623/22 |
| 4,664,668 | 5/1987 | Beck et al. | 623/23 |
| 4,698,063 | 10/1987 | Link et al. | 623/23 |
| 4,718,915 | 1/1988 | Epinette | 623/23 |
| 4,718,916 | 1/1988 | Morscher | 623/23 |
| 4,728,335 | 3/1988 | Jurgutis | 623/23 |
| 4,743,263 | 5/1988 | Petrtyl et al. | 623/23 |
| 4,753,657 | 6/1988 | Lee et al. | 623/16 |
| 4,778,475 | 10/1988 | Ranawat et al. | 623/23 |
| 4,790,852 | 12/1988 | Noiles | 623/23 X |
| 4,813,962 | 5/1989 | Deckner et al. | 623/23 |
| 4,840,633 | 6/1989 | Kallabis et al. | 623/23 |
| 4,842,606 | 6/1989 | Kranz et al. | 623/23 |
| 4,846,839 | 7/1989 | Noiles | 623/18 |
| 4,881,536 | 11/1989 | Noble et al. | 623/22 X |
| 4,883,492 | 11/1989 | Frey et al. | 623/23 |
| 4,904,264 | 2/1990 | Scheunemann | 623/18 |
| 4,904,269 | 2/1990 | Elloy et al. | 623/23 |
| 4,908,035 | 3/1990 | Deckner et al. | 623/23 |
| 4,919,670 | 4/1990 | Dale et al. | 623/23 X |
| 4,936,863 | 6/1990 | Hofmann | 623/23 |
| 4,938,771 | 7/1990 | Vecsei et al. | 623/23 |
| 4,944,759 | 7/1990 | Mallory et al. | 623/22 |
| 4,944,761 | 7/1990 | Stuhmer et al. | 623/23 |
| 4,944,763 | 7/1990 | Willert et al. | 623/23 |
| 4,944,764 | 7/1990 | Stossel | 623/23 |
| 4,979,958 | 12/1990 | Niwa et al. | 623/23 |
| 4,983,183 | 1/1991 | Horowitz | 623/23 |
| 5,002,578 | 3/1991 | Luman | 623/23 |
| 5,018,285 | 5/1991 | Zolman et al. | 623/23 X |
| 5,021,063 | 6/1991 | Tager | 623/23 |
| 5,035,717 | 7/1991 | Brooks | 623/23 X |
| 5,041,141 | 8/1991 | Ypma et al. | 623/23 |
| 5,092,900 | 3/1992 | Marchetti et al. | 623/23 |
| 5,133,770 | 7/1992 | Zweymuller et al. | 623/23 |

FOREIGN PATENT DOCUMENTS

| | | | |
|---|---|---|---|
| 0385585 | 9/1990 | European Pat. Off. | 623/23 |
| 3132543 | 6/1982 | Fed. Rep. of Germany | 623/23 |

OTHER PUBLICATIONS

Gallinaro, P. et al., "Variable Geometry for Proximal Femoral Fixation", in *Joint Replacement: State of the Art*, Coombs, R. et al., eds., Mosby-Year Book Inc. (1990), pp. 113-116.

(List continued on next page.)

*Primary Examiner*—Ronald Frinks
*Attorney, Agent, or Firm*—Browdy & Neimark

[57] ABSTRACT

A femoral component of a hip endoprosthesis includes a lateral supporting wedge designed to be supported by the proximal lateral femur when in use. The wedge can be an integral part of the material of the femoral component or it can be placed on a standard component by cementing or preferably by a male/female socket fit. The lateral surface of the wedge forms an angle of about 10°-20° with the midline of the distal portion of the stem and has an anterior-posterior width of about 8-30 mm, preferably about 10-20 mm, and a medial-lateral extension of the lateral surface of the stem of at least 10 mm, preferably 10-30 mm.

27 Claims, 4 Drawing Sheets

OTHER PUBLICATIONS

Osteonics X-ray analysis templates CDH stems, stem 6A 13% angulation and stem 6B 9% angulation, Osteonics Corp., 1988.

Koch, J. C., "The Laws of Bone Architecture", *Am. J. Anat.*, vol. 21, No. 2, Mar. 1917, pp. 177–298.

Calandruccio, R. A., "Arthroplasty of hip", in *Campbell's Operative Orthopaedics*, vol. 2, Ch. 41, pp. 1213–1501, St. Louis, C. B. Mosby, 1987.

Turek, S. "The Hip", in *Orthopaedics*, ed. 4, Philadelphia, J. B. Lippincott, 1984.

Dow Corning Wright Custom Hip Products, from catalog.

The Intermedics APR Universal Hip System.

Thackray Reconstructive Systems.

Tri-Wedge Porous Coated Hip System.

Cementless poro metal total hip prosthesis, by Professor R. Judet.

Mecron Mr-Cementless Hip Prosthesis.

The S-Som Total Hip System.

Mattory Head Total Hip Program.

Dow Corning Wright Whiteside Total Hip System.

Tech Media Custom Implant Systems.

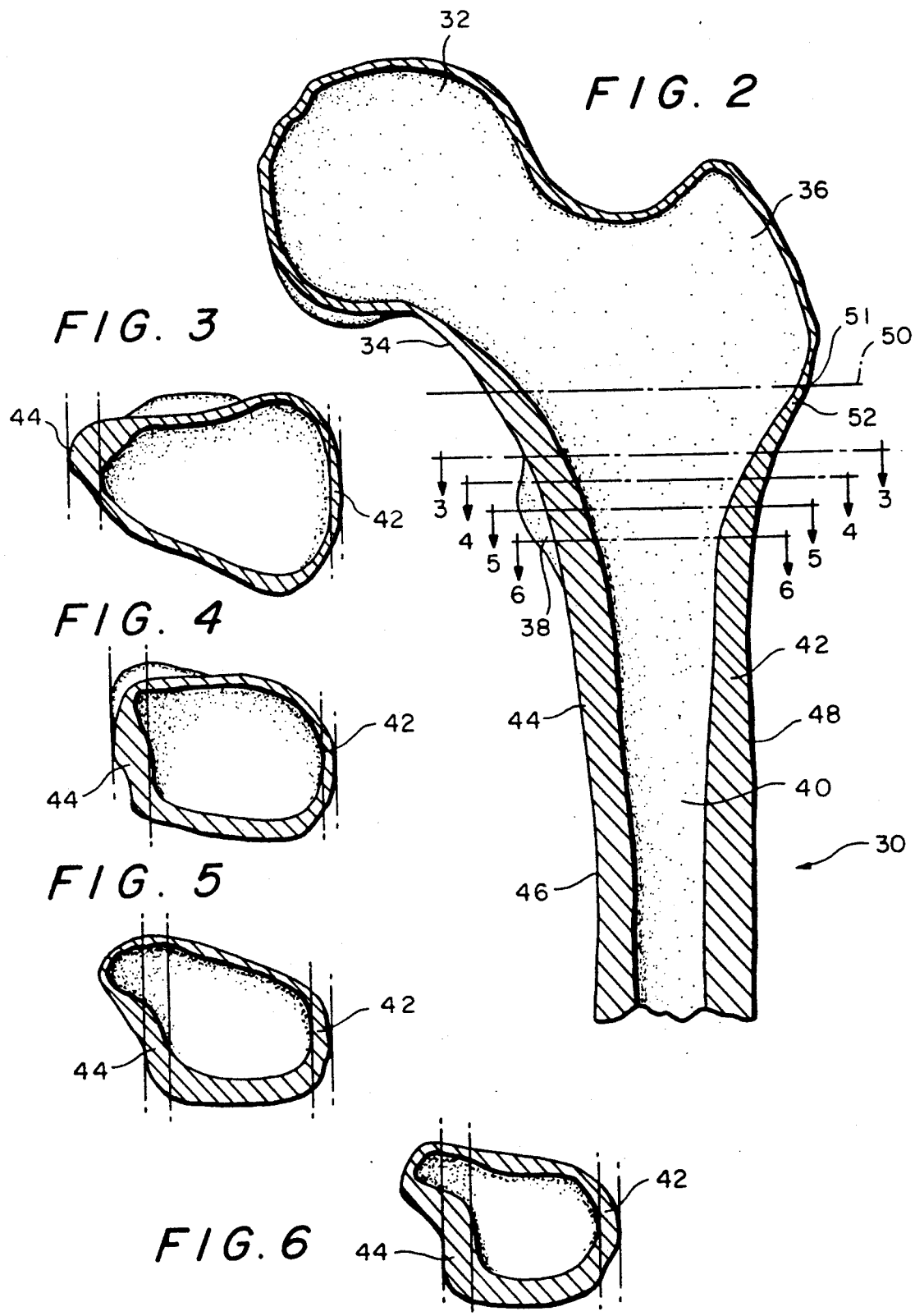

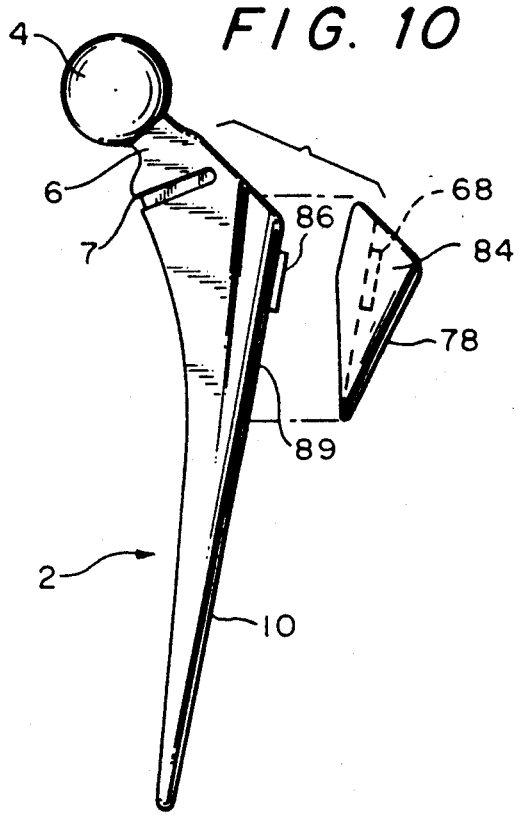
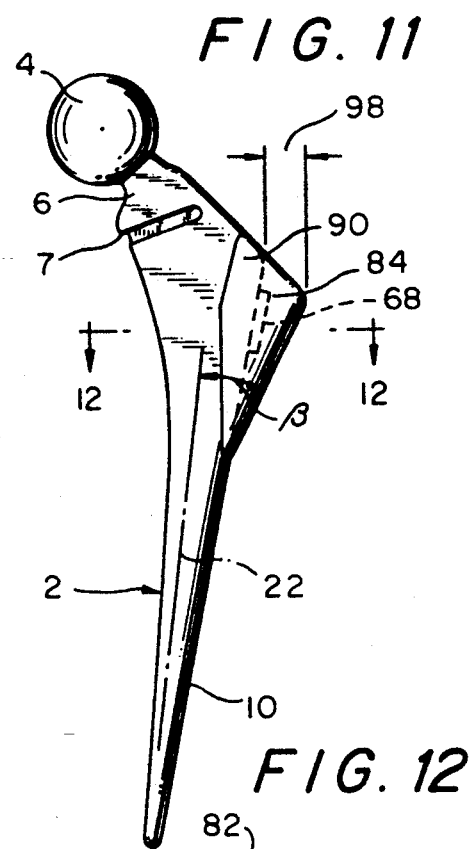
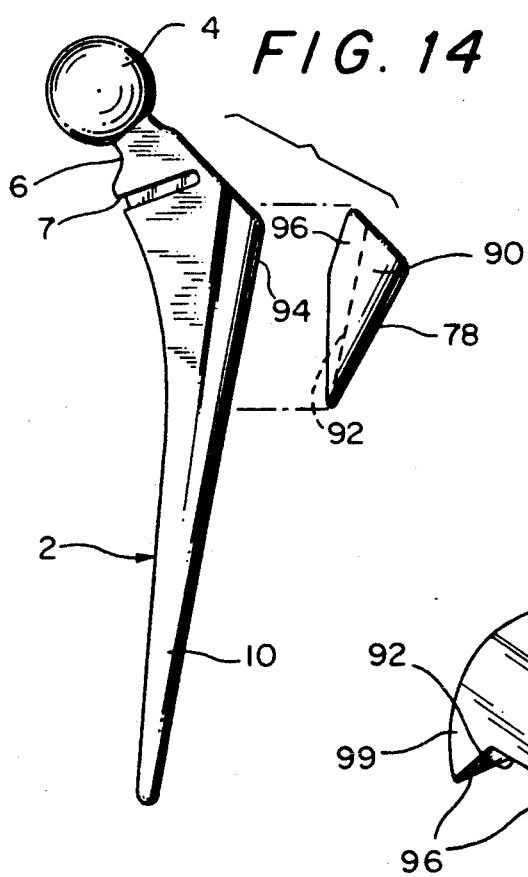
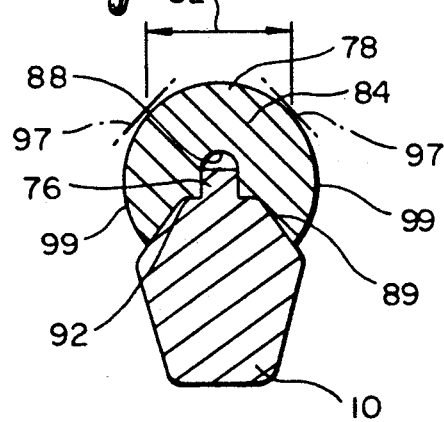
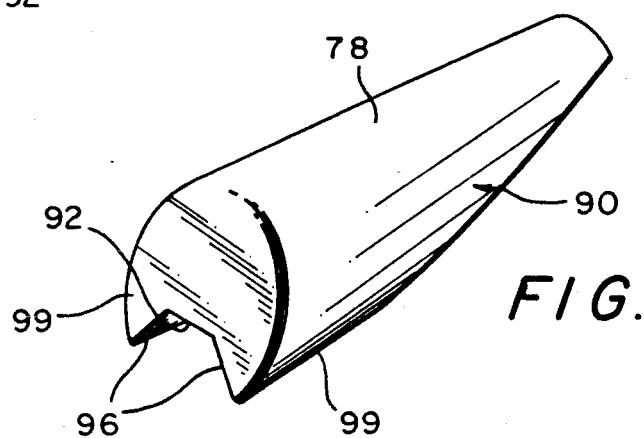

HIP JOINT FEMORAL COMPONENT ENDOPROSTHESIS WITH A LATERAL LOAD-TRANSFERRING SUPPORT SURFACE

FIELD OF THE INVENTION

The present invention relates generally to improvements in prosthetic devices, particularly hip prostheses. More specifically, the present invention relates to an improved prosthesis comprising the addition of a lateral load-transferring support surface designed to rest against the lateral femur when in use. The support surface can be an integral part of the material of the femoral component or it can be in the form of a wedge placed on a standard component by cementing or, preferably, by a male/female socket fit.

BACKGROUND OF THE INVENTION

Artificial or prosthetic devices for replacing defective joints in humans, particularly the hip joint, have been the subject of extensive research and development efforts for many years. In total hip arthroplasty, the most common adult reconstructive hip procedure currently performed in the U.S., a metallic femoral component is typically inserted into the natural medullary cavity of the femur. Simultaneously, an acetabular cup, usually of highdensity polyethylene, is inserted into the acetabulum.

A typical prior art femoral component 2 is shown in FIG. 1. The component 2 is an integral metallic component having a head 4, a neck 6 and a stem 10 having a medial side 11 and a lateral side 13. There is usually a collar 7 between the neck 6 and the stem 10. The medial extension of the collar 7 is the platform 8. The stem 10 has a proximal end 19 and a distal end 20 which ends at the tip 22. Various means of measuring such femoral components are used. The neck length 12 is measured from the center 18 of the head 4 to the base of the collar 7. The head-stem offset 14 is measured from the center 18 of the head 4 to the line 22 through the axis of the distal part 20 of the stem 10. The stem length 16 is measured from the medial base of the collar 7 to the tip 22 of the stem 10. The angle $\alpha$ of the neck 6 is measured by the angle at the intersection of the line 24 through the center 18 of the head 4 and the neck 6 with another line 26 along the lateral border of the distal half 20 of the stem 10.

The femoral component may be made of any strong inert material. Materials which have been used in the past on such components include stainless steel, chromium cobalt molybdenum alloy (Co—Cr—Mo), titanium, or a combination such as Co—Cr—Mo with a ceramic head or titanium with a cobalt-chromium or ceramic head. It may also be made of isoelastic polyacetate.

The head diameter is usually either 22, 26, 28, 32, or 38 mm with a neck length of 30–42 mm. The cross-section of the neck may be round, oval, or trapezoidal. The collar itself may or may not be present. The surface of the stem may be polished, dull, pre-coated with cement, press-fit, or have a porous-metal coating. There may or may not be fenestrations in the stem. The proximal third of the stem may be curved or angulated. The stem may be sabre-shaped, tapered, have a straight lateral edge or an anterior bow or a wide proximal third. The head-stem offset is generally 38–45 mm and the length is generally 12–18 cm or longer. Sometimes the femoral component is made as a modular system with a tapered metal post on the stem to mate with a head component that makes for different neck lengths and diameter of heads made of cobalt-chrome or ceramic. Reference is made to Calandruccio, R. A., "Arthroplasty of Hip" in *Campbell's Operative Orthopaedics* Vol. 2, St. Louis, C. B. Mosby, 1987, chapter 41, pages 1213–1501.

A major problem from which most prior art femoral components suffer is stability of the component in place. Lack of complete stability can cause pain, failure of the artificial hip, fracture of the femur, or various other problems. Many attempts have been made to avoid such problems and add stability. One such attempt is the use of grouting medium or bone cement to fix the femoral component to the bone. In this case, bone is cleared from the medullary cavity to produce a larger space than required for the stem. Grouting material is inserted to fill the gap between the bone and the stem, as a means for fixing the device and as a means for load transfer between the device and the remaining bone.

While such a method is advantageous in that accurate insertion into the bone is not required and immediate mechanical fixation can be achieved leading to early weight bearing and rehabilitation, many disadvantages result from the inherent weakness of the cement which is exacerbated by poor distribution and/or contamination by blood during surgery.

Efforts have been made to fix implants without the use of a grouting medium, in which case it is important that an accurate bone resection be performed. The femoral component must be selected to give the tightest fit possible to provide a mechanically stable support for physiological loading.

Sometimes the surface of the implant is treated to provide a porous or roughened structure which acts to promote bone tissue growth around the implant, further stabilizing the femoral component with respect to the bone.

A major advantage of the latter system is the absence of cement or grouting medium, thus eliminating the long term inherent weakness and the short term toxic effects of these materials. The disadvantages are numerous. First, these stems have the added requirement of a sufficiently tight fit to prevent motion between metal and bone. Accurate bone resection customized to each type of available implant is difficult to achieve and often results in some initial looseness or lack of support. The implant will subsequently migrate to a more stable position, which may not be the ideal orientation for proper function of the femoral component. The requirement for a tight fit increases the possibility of fracture of the femur during insertion. Additionally, the patient must avoid bearing full weight on the hip for approximately six weeks to allow for bone formation.

Treatment of the implant to form the porous or roughened surfaces may cause local stress sites in the implant which significantly increase the risk of fatigue fractures. Further, a considerable time is required for bone tissue ingrowth and stabilization of the implant to occur. This is a significant detriment to early patient rehabilitation. Additionally, surface treatment exposes a greater surface area of the implant, increasing diffusion of metal ions which are associated with an increased risk of toxic or pathological effects.

The implant's stem may weaken from improper stress loads or decreased fatigue strength due to surface treatment. If this happens, the stem may bend or fracture, requiring its removal, which is particularly difficult if significant bone growth has occurred.

Various efforts have been made to design a femoral component hip-endoprosthesis that can be implanted in the medullary canal in such a way as to provide implant stability without resorting to surface treatment. Some such efforts are directed to creating an isoelastic femoral component which is adaptable to the shape of the cavity created for the prosthesis in the femur and thus transfers the load from the implant outward to the bone surrounding the femoral component in the medullary canal. See, for example, U.S. Pat. No. 4,743,263. Other implants use stepped projections (U.S. Pat. No. 4,031,571) or fixation wires (U.S. Pat. No. 4,530,114) to impose tensile forces on the lateral side of the femoral component in the medullary canal. This is reportedly done to anchor the femoral component while taking advantage of the natural conditions of the bone.

Other efforts to stabilize implants have been directed to adding pins or studs (U.S. Pat. No. 3,896,505), wing-like extensions to prevent rotation of the shank (U.S. Pat. No. 4,664,668), plates to provide anti-rotation stability for the implants (U.S. Pat. No. 4,904,269) and anti-rotation fins (U.S. Pat. No. 4,936,863). All of these efforts are directed to preventing the femoral component from rotating inside the medullary canal after insertion as force is applied to the implant by the patient returning to his or her feet.

Most of these implants suffer the disadvantage of prosthesis dislocation and bone fracturing due to improper force distribution on the femur.

Prior to the present invention, all implants have been designed based on the conventional assumption that the lateral femur is under tensile stress when unilateral loading forces are applied to the femur head. This assumption is based on the standard model for describing the biomechanics of the human hip described in the classic work of Koch, published in 1917 (Am. J. Anat. 21:177, 1917). He determined that the medial aspects of the femur are under compressive load during unilateral load, such as during a stride, and most of the lateral cortex is under tensile loading. In Koch's model, most of the force generated within the hip is attributed to the load of the abductor muscles, anatomically defined as taking origin from the lateral aspect of the iliac crest of the hip bone and inserting on the greater trochanter of the femur. Thus, the superimposed body weight creates a lever across the head of the femur, which serves as a fulcrum, with the body weight force being balanced by the abductor muscle force. This model leads to the conventional wisdom that the lateral aspects of the upper femur are under tensile loading.

SUMMARY OF THE INVENTION

It is an object of the present invention to design a femoral component-hip endoprosthesis based on the more accurate model of hip biomechanics which establishes that the lateral aspects of the upper femur are under natural compression loading during the normal activities of standing and walking.

It is another object of the present invention to provide a femoral component having a lateral load-transferring surface which can transfer load to the internal lateral surface of the femur.

It is a further object of the present invention to provide such a femoral component in which said load-transferring surface is part of a lateral support wedge disposed at the upper lateral face of the femoral component stem.

It is yet another object the present invention to provide such a femoral component in which the lateral support wedge is integrally formed with the stem.

It is yet a further object of the present invention to provide such a femoral component in which the lateral support wedge is formed independently from the stem and then attached thereto, preferably with a male/female joint These and other objects of the present invention have been attained due to the present inventor's discovery that the Koch standard model of hip biomechanics, upon which the design of all previous hip endoprostheses have relied, is incomplete and hence its conclusions regarding loading patterns are inaccurate. By using the more complete model of the biomechanics of the human hip developed by the present inventor, improvements in hip prostheses are accomplished which overcome the problems confronting the field.

The femoral component of the present invention is based on the discovery of the present inventor that the lateral aspects of the upper femur are under a compressive load, rather than a tensile stress as predicted by Koch. Thus, both the medial and lateral internal surfaces of the femur may be used as support surfaces for the femoral component. Accordingly, the femoral component of the present invention includes a lateral load-transferring support surface which is supported by the internal lateral surface of the upper femur when in use. The load transferring support surface is part of a wedge-shaped appendage on the lateral side of the proximal portion of the stem of the femoral component. This wedge-shaped appendage may be integral with the stem or may be formed separately and attached to a conventional femoral component by cement, screws, male/female socket fit or any other appropriate manner.

With knowledge that the lateral load-supporting surface will contact the internal lateral surface of the femur under compression at all times, the compressive load on the femoral component can be redistributed onto both sides of the femur to allow a safe and stable setting of the femoral component within the femur.

BRIEF DESCRIPTION OF THE DRAWINGS

The accompanying drawings illustrate the invention. In such drawings:

FIG. 2 is a longitudinal cross-sectional view of a femur.

FIG. 3 is a transverse cross-sectional view along lines 3—3 of FIG. 2.

FIG. 4 is a transverse cross-sectional view along lines 4—4 of FIG. 2.

FIG. 5 is a transverse cross-sectional view along lines 5—5 of FIG. 2.

FIG. 6 is a transverse cross-sectional view along lines 6—6 of FIG. 2.

FIG. 10 is a side elevational view of a femoral component with a conventional stem and a supporting lateral wedge attachable by a male/female joint.

FIG. 11 is a side elevational view of the femoral component of FIG. 10 in assembled condition.

FIG. 12 is a transverse cross-section of the assembled femoral component of FIG. 12 along line 12—12.

FIG. 13 is a perspective view of a wedge usable in the embodiment of FIGS. 10 and 12.

FIG. 14 is a side elevational view of a femoral component with a conventional stem and a supporting lateral wedge attachable using glue or cement.

DETAILED DESCRIPTION OF PREFERRED EMBODIMENTS

Figure 1:
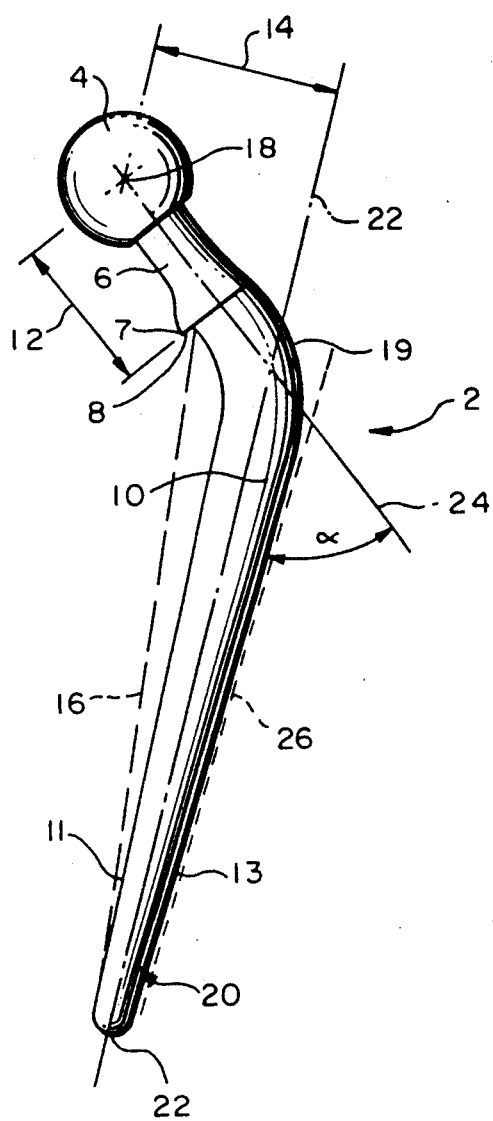
FIG. 1 is a side view of a conventional prior art femoral component.

The embodiment of the present invention will now be described, by way of example, the scope of the invention being indicated in the claims.

As indicated above, previous models of the biomechanics of the hip ascribe most of the force generated within the hip to the load of the abductor muscles. These models have substantially ignored the effect of the fascia lata/ilio-tibial band (ITB). This soft tissue connects the greater trochanter of the femur to the lateral portion of the proximal tibia and essentially functions as a guy wire. It reduces the tensile strains in the proximal femur by acting as a lateral tension band. The result is a compressive load throughout the femur.

Bone is not nature's optimal substance with which to resist tensile forces. Uncalcified collagen, i.e., tendon, has equal tensile strength to bone, with less weight. If the lateral aspect of the femur were under a purely tensile load, it would theoretically be composed of poorly calcified or uncalcified material, rather than relatively thick cortical bone. However, both radiological imaging and cadaveric dissections show relatively thick lateral cortical bone structure.

The proximal half of a human femur 30 is shown in FIG. 2. The femur is comprised of the head 32, the neck 34, the greater trochanter 36, the lesser trochanter 38 and the medullary canal 40. The medial side 46 is the side of the femur 30 facing the midline of the body and the lateral side 48 is the side of the femur 30 toward the outside of the body. The cross-section of FIG. 3 is taken approximately 10 mm distal from the distal limit of the greater trochanter-forming wafer corresponding approximately to the level of the apophyseal scar 51, shown by line 50. The cross-sections of FIGS. 4, 5, and 6 are each approximately 5 mm distal to the previous cut.

Cadaveric transsections of five human femora were made at the levels of lines 3—3, 4—4, 5—5 and 6—6 and the width of the medial and lateral cortical bone present was measured. The measured widths of the medial 44 and lateral 42 cortical bone at the cross-sections of FIGS. 3–6 are shown in Table I.

TABLE I

|  | measured medial cortical bone (range) | measured medial cortical bone (mean) | measured lateral cortical bone (range) | measured lateral cortical bone (mean) |
|---|---|---|---|---|
| FIG. 3 | 5.5–7.0 | 6.2 | 0.5–1.0 | 0.9 |
| FIG. 4 | 5.0–7.5 | 6.0 | 2.0–3.0 | 2.5 |
| FIG. 5 | 5.2–7.0 | 6.14 | 2.5–4.5 | 3.3 |
| FIG. 6 | 4.0–7.5 | 6.0 | 3.5–5.0 | 4.4 |

It can be seen that there is a significant amount of cortical bone mass in the lateral aspect 42 of the femur. This cortical bone mass begins with the inferior lateral aspect 52 of the greater trochanter 36 and coincides with the level of the apophyseal scar 51. The width of this cortical bone increases so that by 10 mm distal to the apophyseal scar, a point at approximately the level of the superior aspect of the lesser trochanter 38, it is more than 40% that of the medial cortex 44. With additional 5 mm increments, this lateral thickness increases to 50% and 73% of the medial cortical width, respectively. This ratio remains approximately constant with further distal sectioning of the femur, reducing only as one approaches the distal femur at the level of the lateral femoral epicondyle. These observations are consistent with the theory that the lateral aspect of the femur is under compressive load rather than tensile stress.

Thus, a model of the hip which includes the tension band effect of the ITB is consistent with femur bone morphology.

Figure 7:
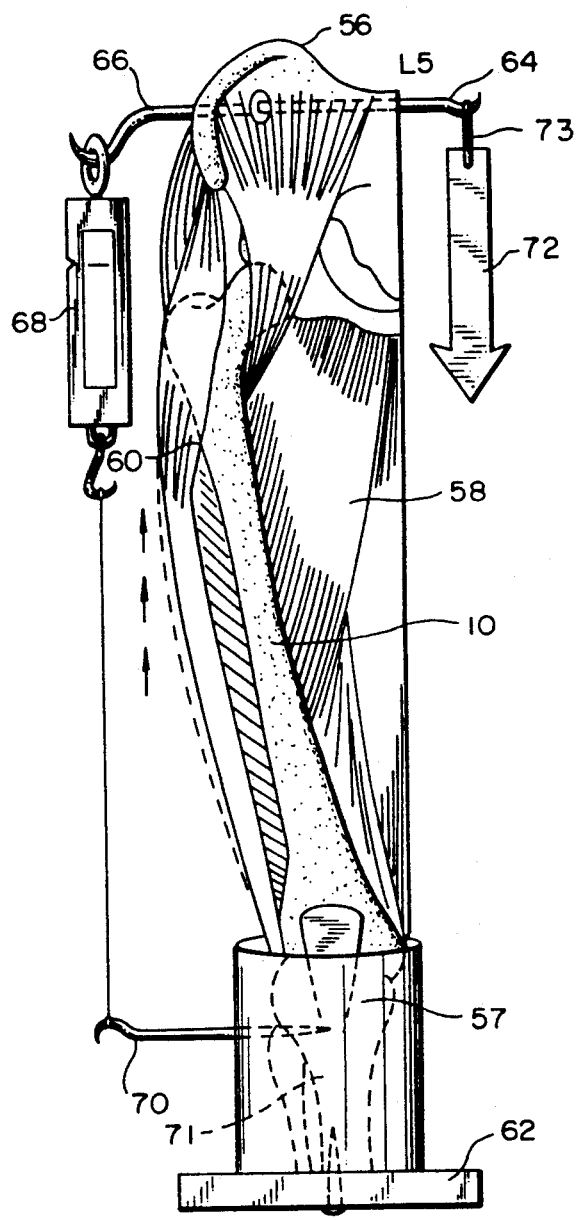
FIG. 7 is a front elevational view of a cadaveric dissection mounted on a test stand for performing a static test of the lateral fascial band.

In order to further demonstrate the effect of the ITB, a test was conducted of the static cadaveric loading of the human hemipelvis. The set-up for this test is shown in FIG. 7. A male cadaver was hemisected at L4 then sagittally sectioned through the pelvis 56. The leg was transected approximately 8 cm distal to the knee joint 57. The quadriceps femoris, including rectus femoris and sartorius muscles, were removed. The adductor muscles 58, hamstrings, iliopsoas, tensor fascia lata 60, gluteus maximus and gluteus minimus were left intact as were the smaller rotators of the hip joint. The gluteus medius was transected at its insertion on the greater trochanter and femur.

The specimen was mounted vertically on static test stand 62, approximately at the anatomic position of the leg in its normal seven degrees of knee valgus standing position, as shown in FIG. 7. A steel hook 64 was affixed at L5, and another hook 66 was placed through the ileum, projecting laterally.

A spring scale 68 was attached from the lateral pelvic hook 66 and anchored to another hook 70 which was secured to the tibia 71 approximately 4 cm below the knee joint 57, so as to parallel the lateral fascial band of the thigh (ITB). Serial weights 72 were attached by chain 73 to the pelvic hook 64 and the load registered on the lateral spring scale 68 was recorded. When the cadaveric specimen was serially loaded with weights of 2.2, 4.5 and 6.8 kg, a tensile force of 0.7, 1.5 and 2.3 kg was observed in the spring scale. This resistance was sufficient to prevent varus displacement and to maintain the equilibrium state during pelvic loading. Thus, when loading at the body's theoretical center of gravity, the ITB maintained a medial-lateral equilibrium state across the hip joint by exerting a tensile resistance. The efficiency of this resistance required the ITB to experience a ⅓ kg of tensile load for each kg of downward load applied to the pelvis. It was noted that the gluteus medius, having been sectioned, was not necessary for this equilibrium state to be maintained.

This model demonstrates, therefore, how lateral compressive loading does occur in the proximal femur and why there is such a significant amount of cortical bone mass in this region.

Mathematical analysis of the forces involved, when including the tension band effect of the ilio-tibial band, also confirms that the proximal-lateral aspect of the femur is under compressive load on unilateral stance rather than the previously expected tensile load.

Figure 8:
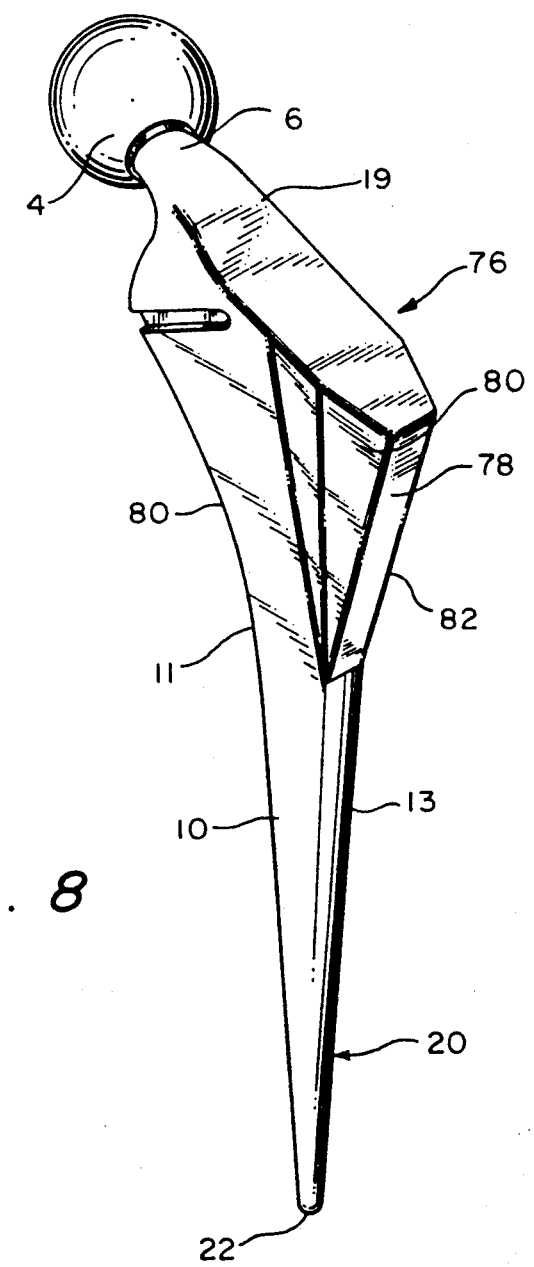
FIG. 8 is a perspective view of one embodiment of a femoral component of the present invention.
Figure 9:
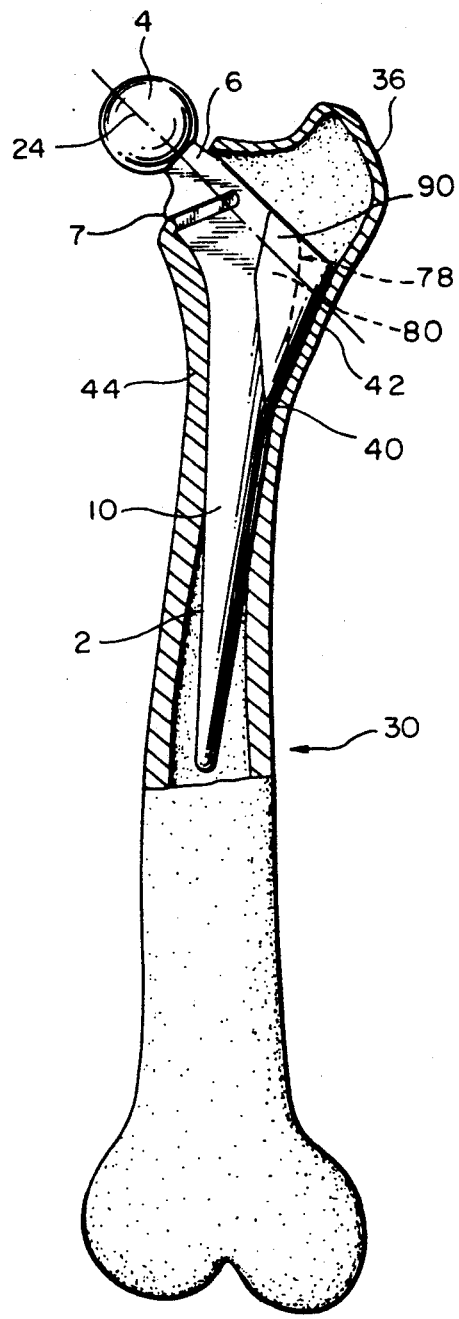
FIG. 9 is a side elevational view, partially broken away, of a femur with the femoral component of the present invention inserted in the medullary canal.

The hip endoprosthesis femoral component of the present invention was designed to take full advantage of this new knowledge that the proximal lateral cortex of the femur is under compressive load during unilateral stance. As seen in FIG. 8, the component 76 is designed with a lateral load transferring support surface 78 which contacts and rests on the lateral femur when in place (see FIG. 9), thus preventing subsidence and rotation after emplacement and distributing the loading forces more naturally along the femur.

By providing such improved stability and load distribution, there will be fewer prosthesis failures, less bone damage and subsequently fewer bone fractures.

In the embodiment of FIG. 8, the lateral support surface 78 is part of a wedge 80 fully integrated into the prosthesis 76. The femoral component 76 is otherwise conventionally comprised of a head 4, neck 6, and a stem 10 having a medial side 11, a lateral side 13, a proximal end 19, and a distal end 20. While no collar is present in the embodiment of FIG. 8, such may optionally be present.

The lateral support surface 78 should be large enough in conjunction with the stem 10, to transfer all lateral loading forces onto the upper third of the femur 30. The stem 10 and wedge 80 should form a tight proximal fit in the medullary canal 40 when downward force is applied. The downward force applied to the head 4 of the endoprosthesis will be transferred through the neck 6, stem 10 and lateral support wedge 80. The force will be subsequently distributed onto the medial cortex 44 and lateral cortex 42 of the femur 30. The force will be entirely compression force and not tensile or pulling force.

The lateral support surface 78 is not designed to penetrate or otherwise compromise the cancellous bone of the trochanter 36 either by a crushing or cutting action. Rather, the lateral support surface 78 is designed to rest against the lateral cortex 42 of the bone shaft. The lateral support wedge 80 is a fixed part of the endoprosthesis It can be manufactured as one component, as in the embodiment of FIG. 8, or a retro-fit of a standard prosthesis as in the embodiments of FIGS. 10-14. The entire device 76 is inserted at one time.

As shown in FIGS. 10-13, the lateral support wedge 84 is manufactured as a separate entity which can be emplaced on a conventional femoral component 2 such as that shown in FIG. 1. In this embodiment, the support wedge 84 is maintained on the stem 10 by means of a male plug 86 disposed at the appropriate location on the proximal portion of the lateral stem 10 and a female socket 88 in the medial surface 92 of the wedge 84. This can be particularly seen in cross-sectional view of FIG. 12. The wedge 84 preferably includes side wings 90 which extend beyond the lateral surface 89 and are shaped to correspond in shape to the corresponding surface of the stem 10. This provides additional contact surface between the wedge 84 and the stem 10. The placement of the wedge 84 on the surface 89 of the stem 10 can be further enhanced by means of an adhesive such as glue or cement.

Wedges 84 can be manufactured in various shapes and sizes so that the surgeon can select the appropriate combination of stem 10 and wedge 84 to make an appropriate prosthesis for the particular femur being fitted.

In FIG. 14, wedge 91 is also manufactured as a separate component but without the female socket 88 as is used on the wedge 84 of FIGS. 10-13. Similarly, no male plug B6 need be disposed on stem 10. In the embodiment of FIG. 14, the lateral support wedge is affixed to the surface 94 of the stem 10 solely by means of an appropriate adhesive, such as glue or cement. The medial surface 92 and the internal surfaces of the wings 96 of the wedge 9 are designed to match and attach to the lateral surface 94 of the stem 10.

In all of the embodiments of the present invention, the lateral support surface 78 should have an anterior-posterior (A-P) width 82 which is large enough to provide sufficient support when contacting the internal surface of the lateral cortical bone, without acting as a stress riser which might violate or compromise the integrity of the bone. Preferably, the A-P width 82 of the support surface 78 should be at least 8 mm, preferably 10-20 mm, although it may be as wide as 30 mm. The use of the terms anterior, posterior, medial and lateral with respect to a femoral component throughout the present specification and claims refers to the respective directions when the component is in place in a human femur, as designed. If the A-P width of the support surface 78 is too narrow, such as the width of the rotation preventing fins in the prior art, then it will act as a knife and cut the bone rather than transfer the load forces. The width 82 may be substantially the same as the medial support surface of the stem below the collar 7.

The support surface 78 of the wedge 80 is preferably slightly rounded so as to approximate the radius of curvature of the internal geometry of the lateral surface of the medullary canal from about the level of the lesser trochanter to about the level of the apophyseal scar, such as is shown in the embodiments of FIGS. 9-14. Such a curvilinear surface gives better surface contact, thus permitting superior load transmission. Furthermore, because of the anterior-posterior contact with the internal femoral cortex at the edges of the bulge 99 at the sides of the wedge 84, additional anti-rotational or torsional support is obtained. When the support surface 78 is rounded, the A-P width 82 is measured as a cross-section between the points 97 (see FIG. 12) on the surface of the wedge at which the tangent to the curve forms an angle of 45° with the horizontal.

The medial-lateral (M-L) breadth 98 of the wedge 84 from the surface 92 to the lateral surface 78 at its broadest point (see FIG. 11) should be at least 10 mm, preferably 10-30 mm, most preferably 15-20 mm. In the embodiment in which the wedge 80 is integral with the stem 10, the M-L breadth is measured in a corresponding manner, i.e., it extends what would otherwise have been the lateral surface of the stem by at least 10 mm. This breadth is optimal for the prevention of subsidence of the component when in use, over the course of time.

The angle $\beta$ between the support surface 28 and the midline 22 of the distal stem 20 is about 5°-20°, preferably about 10°-15°. Such an angle permits optimal transfer of the lateral loading forces onto the femur.

While some prior art prostheses have a lateral surface which is incidentally at an angle of about 5°-20° with the midline of the distal stem, this has always been for reasons other than serving as a lateral support surface, which is the purpose of the present invention. Such prior art prostheses have other elements which are critical to the disclosed purpose for the lateral surface angle in the prior art, usually to create some sort of load transfer to the anterior and posterior intertrochanteric region of the femur when in use, particularly at the medial and central portions of the A-P surfaces. For example, U.S. Pat. No. 4,840,633 to Kallabis et al discloses a femoral endoprosthesis which utilizes a screw spindle with a broad-flanged helical flank. The purpose of the flank is to project outwardly from both side faces of the stem and cut into the cortex of the anterior and posterior internal bone structure of the femur for improved proximal load transmission. To make room for the helical flank, the lateral surface of the proximal stem extends at an angle to the midline of the distal stem which may be within the range contemplated by the present invention. However, the present invention does not need a helical flank and such is to be expressly avoided in the present invention. Without such a helix, Kallabis et al would teach no reason to include a lateral surface with such an angle.

Similarly, the femoral endoprosthesis of U.S. Pat. No. 4,659,067 to Fournier, shows a lateral surface which appears to have an angle of about 10°. However, the lateral surface comes to a point and does not include a load-bearing surface. Thus, this device is similar to the devices with thin anti-rotational fins (such as U.S. Pat. No. 4,936,863). Furthermore, Fournier requires oblique load-transfering projections on the anterior and posterior faces which are not included in the present invention.

U.S. Pat. No. 4,778,475 to Ranawat et al discloses a femoral endoprosthesis with a wedge-shaped proximal portion in the intertrochanteric region which engages, for load transmission, the anterior and posterior endosteal surfaces of the femur, across the entire medial-lateral width thereof. Thus, the intention of Ranawat is to transmit loads to the anterior and posterior femoral surfaces, which is contrary to the present invention which is designed to transmit loads to the medial and lateral femoral surfaces. The neck of Ranawat extends obliquely medially, anteriorly and superiorly from the proximal portion. This patent erroneously states that the bone is under tension at the proximal lateral aspect. Indeed, the design is intended to minimize load transfer apart from the lateral distal tip and the region generally corresponding to the porous-coated recess shown in FIG. 7 of Ranawat. Because of the unusual oblique angle of the neck to the stem it is difficult to measure the angle of the proximal lateral surface to the midline of the distal stem. However, the present invention expressly avoids the use of a wedge shape of the anterior and posterior faces of the proximal stem at the medial and central portions thereof as well as the oblique angularity of the plane of the neck with the plane of the stem. Without these unusual features of Ranawat et al, there would be no reason to utilize a lateral surface with an angle of about 5°–20° with the midline of the distal stem.

As opposed to these prior art prostheses, the femoral component of the present invention needs no structure specifically designed to transfer load to the anterior and posterior intertrochanteric region of the femur when in use. The bulge 99 of the wedge 84, shown particularly in FIGS. 12 and 13, may inherently cause some load transfer to the A-P surfaces of the femoral cortex and this is indeed advantageous as such contact prevents torsional forces. However, there is no such bulge or wedge on the A-P surfaces of the medial and central portions of the proximal stem. This feature clearly distinguishes the femoral component of the present invention from the components shown, for example, in the Kallabis and Ranawat patents.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A femoral component of a hip endoprosthesis for implantation into the upper end of the medullary canal of a femur, said prosthesis comprising:
   a stem having a distal end, shaped and dimensioned for introduction into a medullary cavity of a femur, and a proximal end, said stem having a medial side on the side thereof intended to be adjacent to the medial side of the femur when in use and a lateral side on the side thereof intended to be adjacent to the lateral side of the femur when in use;
   a neck connected to and extending away from the proximal end of said stem, said neck being adapted to be connected to a head means for functioning as a femur head when in use; and
   a lateral support wedge integrally formed with or fixedly connected to said stem near the proximal end thereof, and being sized and shaped to extend the lateral side of said stem so as to form a lateral support surface which contacts the proximal lateral femoral cortex of the intertrochanteric region of the femur when in use, said lateral support surface forming an angle of 5°–20° with the midline of the distal portion of said stem and having a sufficient width to permit transfer of the force applied to the head means, when in use, onto the femur such that such contact will not damage the femur, said femoral component having no structure specifically designed to transfer load to the medial and central portions of the anterior and posterior intertrochanteric region of the femur when in use.

2. A femoral component in accordance with claim 1, wherein said lateral support wedge is integrally formed with said stem as one piece.

3. A femoral component in accordance with claim 1, wherein the anterior-posterior width of the lateral support surface is greater than about 8 mm.

4. A femoral component in accordance with claim 3, wherein the anterior-posterior width of the lateral support surface is about 10–30 mm.

5. A femoral component in accordance with claim 1, wherein said lateral support wedge is a separate component which is connected to said stem.

6. A femoral component in accordance with claim 5, wherein said lateral support wedge is connected to said stem by means of a male/female joint.

7. A femoral component in accordance with claim 5, wherein said lateral support wedge is connected to said stem by means of an adhesive.

8. A femoral component in accordance with claim 1, wherein said angle of the lateral support surface is about 10°–15°.

9. A femoral component in accordance with claim 1, wherein the medial-lateral breadth at the broadest point of the lateral support wedge is such that it extends the lateral surface of said stem by at least 10 mm.

10. A femoral component in accordance with claim 1, wherein said lateral support wedge is shaped such that the lateral support surface thereof is slightly rounded so as to approximate the radius of curvature of the proximal lateral femoral cortex with which it is in contact when in use.

11. A femoral component in accordance with claim 10, wherein said lateral support wedge is integrally formed with said stem in one piece.

12. In the method of inserting a femoral component of a hip prosthesis into the femur of a patient undergoing hip joint replacement, comprising placing the femoral component into the medullary canal of the femur, the improvement wherein said femoral component is a femoral component in accordance with claim 1 of a size selected so as to form a tight proximal fit in the medullary canal when downward force is applied, the lateral support surface of said wedge being in contact with the lateral cortex of the intertrochanteric region of the femur to transfer lateral loading forces thereto.

13. A method in accordance with claims 12, wherein all lateral loading forces are transferred onto the upper third of the femur.

14. A femoral component of a hip endoprosthesis for implantation into the upper end of the medullary canal of a femur, said prosthesis comprising:

a stem having a distal end, shaped and dimensioned for introduction into a medullary cavity of a femur, and a proximal end, said stem having a medial side on the side thereof intended to be adjacent to the medial side of the femur when in use and a lateral side on the side thereof intended to be adjacent to the lateral side of the femur when in use;

a neck connected to and extending away from the proximal end of said stem, said neck being adapted to be connected to a head means for functioning as a femur head when in use; and a separate discrete lateral support wedge fixedly connected to said stem near the proximal end of said stem so as to extend the lateral side of said stem, when in use, so as to form a lateral support surface which contacts the proximal lateral femoral cortex in the intertrochanteric region of the femur, said lateral support surface having a sufficient width to permit transfer of the force applied to the head means, when in use, onto the femur such that such contact will not damage the femur.

15. A femoral component in accordance with claim 14, wherein the anterior-posterior width of the lateral support surface is at least about 8 mm.

16. A femoral component in accordance with claim 15, wherein the anterior-posterior width of the lateral support surface is about 10–30 mm.

17. A femoral component in accordance with claim 14, wherein said lateral support wedge is connected to said stem by means of a male/female joint.

18. A femoral component in accordance with claim 14, wherein said lateral support wedge is connected to said stem by means of an adhesive.

19. A femoral component in accordance with claim 14, wherein said lateral support surface forms an angle of 5°–20° with the midline of the distal portion of the stem.

20. A femoral component in accordance with claim 19, wherein said angle of the lateral support surface is about 10°–15°.

21. A femoral component in accordance with claim 19, wherein the medial-lateral breadth of the lateral support wedge from the medial surface thereof in contact with the lateral surface of said stem to the lateral surface of said wedge at the widest point thereof is at least 10 mm.

22. A femoral component in accordance with claim 14, wherein the medial-lateral breadth of the lateral support wedge from the medial surface thereof in contact with the lateral surface of said stem to the lateral surface of said wedge at the widest point thereof is at least 10 mm.

23. A femoral component in accordance with claim 14, wherein said separate lateral support wedge is shaped such that the lateral support surface thereof is slightly rounded, said wedge having anterior-posterior side surfaces which bulge outwardly with respect to the anterior-posterior side surfaces of said stem, said anterior-posterior side surfaces of said wedge extending medially to form wings which overlap the lateral portion of the anterior-posterior side surfaces of said stem, the interior surface of said wings and the medial surface of said wedge which contacts the lateral surface of said stem having a shape which corresponds with the shape of the corresponding surfaces of said stem.

24. A lateral support wedge connectable to the proximal end of the stem of a femoral component of a hip endoprosthesis implantable into the upper end of the medullary canal of a femur, said wedge being shaped so as to extend the lateral side of the stem of the femoral component, when in use, so as to form a lateral support surface which contacts the proximal lateral femoral cortex of the intertrochanteric region of the femur, said lateral support surface forming an angle of 5°–20° with the midline of the distal portion of the stem when connected thereto and having a sufficient width to permit redistribution of the force applied to the femoral component, when in use, onto the femur such that such contact will not damage the femur, said wedge having no structure specifically designed to transfer load to the medial and central portions of the anterior and posterior intertrochanteric region of the femur when in use.

25. A lateral support wedge in accordance with claim 24, wherein said said wedge is shaped such that the lateral support surface thereof is slightly rounded and the anterior-posterior side surfaces thereof bulge outwardly with respect to the anterior-posterior side surfaces of the stem to which it is connectable, when in use, said anterior-posterior side surfaces of said wedge extending medially to form wings which overlap the lateral portion of the anterior-posterior side surfaces of the stem to which it is connectable, the interior surface of said wings and the medial surface of said wedge which contacts the lateral surface of the stem when in use having a shape which corresponds with the shape of the corresponding surfaces of the stem to which the wedge is connectable.

26. A lateral support wedge in accordance with claim 24, wherein the medial-lateral breadth of the lateral support wedge from the medial surface thereof in contact with the lateral surface of said stem, when in use, to the lateral surface of said wedge at the widest point thereof is at least 10 mm.

27. A lateral support wedge in accordance with claim 24, wherein said lateral support surface forms an angle of 10°–15° with the midline of the distal portion of the stem when connected thereto.

* * * * *